(12) United States Patent
Webber et al.

(10) Patent No.: US 9,810,611 B2
(45) Date of Patent: Nov. 7, 2017

(54) PROCESSING METHOD AND CASSETTE

(71) Applicant: Cellpath Ltd, Powys (GB)

(72) Inventors: Paul Webber, Powys (GB); Philip Webber, Powys (GB); Richard Titcombe, Powys (GB)

(73) Assignee: Cellpath Ltd., Powys (GB)

(*) Notice: Subject to any disclaimer, the term of this patent is extended or adjusted under 35 U.S.C. 154(b) by 15 days.

(21) Appl. No.: 14/494,022

(22) Filed: Sep. 23, 2014

(65) Prior Publication Data

US 2015/0087019 A1    Mar. 26, 2015

(30) Foreign Application Priority Data

Sep. 23, 2013  (GB) .................................. 1316896.8

(51) Int. Cl.
*A61B 10/00* (2006.01)
*G01N 1/31* (2006.01)
*G01N 1/36* (2006.01)

(52) U.S. Cl.
CPC ............... *G01N 1/312* (2013.01); *G01N 1/36* (2013.01); *G01N 2001/366* (2013.01)

(58) Field of Classification Search
CPC .................................. G01N 1/312; C12M 1/00
See application file for complete search history.

(56) References Cited

FOREIGN PATENT DOCUMENTS

| EP | 0312109 A2 | 4/1989 |
|---|---|---|
| GB | 2278441 A | 11/1994 |
| GB | 2453320 | * 4/2009 |
| WO | WO 2007/073481 A1 | 6/2007 |
| WO | WO 2009-055603 | 4/2009 |

OTHER PUBLICATIONS

Search Report dated Mar. 25, 2014 for Application No. GB 1316896.8 from the United Kingdom Intellectual Property Office.
European Search Report dated Jan. 12, 2015, for EP Application No. 14186039.5-1553 from the European Patent Office.
The Histology Family/Simport Catalogue, Jan. 26, 2011, XP055159570, Retrieved from the Internet: URL:https://web.archive.org/web/19960201000000*/http:// . . . Dec. 18, 2014].

* cited by examiner

*Primary Examiner* — Jyoti Nagpaul
(74) *Attorney, Agent, or Firm* — Cook Alex Ltd.

(57) ABSTRACT

A method of avoiding deformation and providing for a more consistent thickness of a biological tissue sample during preparation for analysis comprising providing a histology processing cassette comprising a box defining a compartment for holding a biological tissue sample, the box having a bottom face comprising a sample support surface and being transmissible to radiation or a flow of fluid through to pass through the cassette, an open top face, and two side walls, a back wall and a front wall, the box having a length and width greater than a standard size histology processing cassette and a depth approximately the same as a standard size histology processing cassette placing the sample in the cassette and treating the sample by contacting it with a processing solution; and contacting the sample with molten paraffin wax and cooling the sample in molten paraffin wax so the sample is embedded in solidified paraffin wax for further processing.

9 Claims, 3 Drawing Sheets

PROCESSING METHOD AND CASSETTE

This invention relates to a cassette, in particular a histology processing cassette suitable for processing biological tissue samples and to a method of treating a biological tissue sample, particularly large tissue samples. The invention relates particularly to a large histology processing cassette suitable for processing large biological tissue samples.

Biological materials for histological examination are processed in large quantities for a wide range of diagnostic purposes. Tissue samples are prepared typically by a process involving embedding the tissue sample in paraffin wax and slicing the embedded sample very thinly using a microtome. Prior to embedding the sample, it is treated using solutions selected according to the nature of the sample. The sample is suitably fixed, dehydrated, cleared, infiltrated with molten paraffin wax and optionally stained. Typical fluids employed in such processing may include ethanol, xylene, formaldehyde and water. Processing in which the sample is contacted with a processing solution and contacted with paraffin wax typically involves cooling and may take place over an extended period, for example overnight. Typically, a large number of samples, for example around 50 are processed together.

Embedding the tissue in paraffin wax provides it with the rigidity necessary for further processing, for example microtome slicing. The processing usually involves placing the material in a small box-like plastics carrier, known in the art as a "cassette".

Known cassettes for processing biological tissues typically comprise an open-topped box with a perforated bottom wall. The box may have a perforated top cover which is moveable relative to the box or a removable perforated cover. The cassette typically has a three vertical side walls and the fourth, side wall, on the front side of the cassette is typically sloping and includes an area for labelling the cassette. The perforations of the box and cover are typically from 1 to 3 mm in diameter. Known processing cassettes are described in GB 1230913 and U.S. Pat. No. 3,674,396.

Known processing cassettes are used with the cover in place as a tissue processing capsule and with the cover removed for embedding a specimen in paraffin wax. The processing cassette defines a cavity, which may be closed with the use of a perforated lid, into which the biological tissue is placed for processing. Generally, processing cassettes define one cavity and process one sample at a time although cassettes having multiple cavities to allow processing of more than one sample are known. Processing cassettes are typically constructed of plastics material and the perforations are made in the plastic material which forms the bottom wall and, where employed, the plastics material forming the lid.

Cassettes of a "standard size" are typically employed as it is required to fit in other apparatus, for example fit standard specimen holders, known as chucks, of microtomes. "standard size" histology processing cassettes typically have internal dimensions of 28 to 32 mm×25 to 28 mm×5 to 6 mm, typically a maximum size of 30 to 31 mm by 25 to 26 mm. Minor variations in size may occur, dependent for example upon the wall thickness of the box.

However, larger samples require the use of a larger cassette and a standard size larger cassette are commonly employed. Typically a larger cassette has a sample compartment which is typically twice the length and twice the width of the sample compartment of a standard size cassette and a depth of twice that of a standard size cassette. A larger cassette therefore has an area approximately four times that of a standard cassette and a volume approximately eight times that of a standard cassette. Typical dimensions of a larger cassette are around 50 to 55 by 65 or 70 to 75 or 80 by 12 to 17 mm. The ratio of the length, to the width and to the depth of a larger cassette is therefore approximately the same as that of a standard sized cassette.

In known larger cassettes, samples may curl or otherwise move prior to or during processing within the volume of the cassette, due to the depth being 12 to 17 mm. This may be problematic from a processing viewpoint and also in ensuring the sample is appropriately oriented for subsequent processing, for example sectioning and microscopy.

Whilst certain samples are of such a size as to require a compartment having a larger area, during processing the sample may curl, deform or otherwise change shape due to contact with processing liquids such as solvents, for example xylene, paraffin wax and alcohol. In a standard sized cassette, such deformation may be constrained by the surface upon which the sample rests and the lid of the cassette. However, the greater depth of a larger sized cassette may not so readily constrain such tendency to deform or curl and this may mean that subsequent processing or analysis, for example lengthways slicing or sectioning of the sample is disadvantageously carried out on only a part of the sample.

We have now devised a larger sized histology processing cassette which addresses the disadvantage of sample deformation during processing whilst accommodating larger samples.

The invention provides in a first aspect a method of avoiding deformation of a biological tissue sample during preparation for analysis comprising:
  i) providing a histology processing cassette comprising a box defining a compartment for holding a biological tissue sample, the box having a bottom face comprising a sample support surface and being transmissible to radiation or a flow of fluid through the face, an open top face, and two side walls, a back wall and a front wall, the box having a length and width greater than a standard size histology processing cassette and a depth approximately the same as a standard size histology processing cassette;
  ii) placing the sample in the cassette and treating the sample by contacting it with a processing solution; and
  iii) contacting the sample with molten paraffin wax and cooling the sample in molten paraffin wax so the sample is embedded in solidified paraffin wax for further processing.

The first aspect of the invention enables a more consistent thickness of specimen to be produced for analysis.

In a second aspect, the invention provides a histology processing cassette comprising a box defining a compartment for holding a biological tissue sample, the box having a bottom face comprising a sample support surface and being transmissible to radiation or a flow of fluid through the face, an open top face, and two side walls, a back wall and a front wall, the box having a length and width greater than a standard size histology processing cassette and a depth the approximately same as a standard size histology processing cassette.

A conventional standard larger cassette generally has a width of 50 to 55 and a length of 65 or 70 to 75 or 80 and a depth of 12 to 17 mm. The ratio of the length to the width is approximately from 7 to 8:5. The ratio of the width to the depth from 3 to 4:1 and the ratio of the length to the depth is from approximately 4 to 6:1.

In the present invention, the cassette generally has a width of 50 to 55 and a length of 65 or 70 to 75 or 80 and a depth of 6 to 8 mm. The ratio of the length to the width is approximately from 7 to 8:5. The ratio of the width to the depth is from 6 to 9:1 and the ratio of the length to the depth is from approximately 9 to 12:1. In a preferred embodiment, the length, width and depth of the cassette are suitably 75, 52.5 and 7 or 8 mm respectively.

The invention also provides a histology processing apparatus comprising, in combination, apparatus for processing or analysing a biological sample and a histology processing cassette according to the first aspect of the invention.

The invention further provides for use of a histology cassette according to the second aspect of the invention in the preparation of a sample for analysis or for analysis of a sample for example by irradiation or a flow of fluid through the face for processing or analysis.

The term "transmissible" as employed herein means that radiation or fluid for processing or analysis is able to pass through apertures or perforations in the face whether a plastics face with apertures or perforations or a gauze.

Advantageously, the invention enables samples to be processed in larger sized cassettes but with reduced risk of deformation of the sample as compared to processing in conventionally dimensioned larger sized cassettes. Further, the smaller overall volume of the cassette enables greater numbers of cassettes, for example double the number of larger sized cassettes typically processed, to be processed in a single run. During processing, cooling of the sample and cassette to solidify the paraffin wax takes energy and a smaller volume of paraffin wax is required to form a solidified sample for subsequent processing thereby providing savings in energy usage per sample analysed during processing.

Suitably the samples being analysed comprise biological tissue samples. The histology processing cassette is adapted to engage with a cassette-receiving site in apparatus for histological examination, processing or analysis of a larger biological tissue sample than is analysed in a standard size cassette.

The compartment for holding biological tissue extends between the top face and the bottom face of the cassette to define one or more compartments for receiving the sample or samples to be analysed. The bottom of the sample compartment and the top of it, for example a lid, are suitably transmissible to X-ray or other radiation and allows transmission of a processing liquid through the bottom and the top of the compartment and suitably comprises perforations in a plastics face or a mesh, for example a polyamide mesh.

The compartment for holding the sample preferably has dimensions of 50 to 55 mm by 65 or 70 to 75 or 80 mm and a depth of 5 to 10 mm, for example 7 or 8 mm. As the depth of the sample compartment in the cassette is significantly shallower than sample compartments in known larger size cassettes, the sample is less able to curl or otherwise move within the compartment and allows for a greater consistency of specimen thickness and drawbacks associated with this are therefore ameliorated.

The box may comprise a single compartment or multiple compartments. Preferably, the compartment is at least 5 mm wide in their smallest dimension parallel to the top or bottom face. Where multiple compartments are employed, the compartments may be any suitable shape, for example elongate and square and may be arranged in any desired manner in the cassette. Preferably, the compartments are arranged to extend across the full width of the cassette. Endoscopy biopsies for example, may be processed in compartments which are more square than elongate.

Suitably, the top face of the cassette is covered by a lid comprising a plastics sheet having perforations and engages releasably with the box of the cassette. Suitably, the lid is moveable relative to the box of the cassette. Preferably the lid is detachable and the lid and box have complementary engaging means, for example, recesses and lugs, to allow secure attachment of the lid to the box. If desired, the lid may be permanently attached to the box and pivotally mounted, for example through a hinge, to the box.

The lid of the box is suitably pivotally mounted on the box and adapted in a first configuration to be open wherein the lid is at an angle to the box of less than 170 degrees, preferably 100 to 140 degrees, and in a second configuration to close the compartment.

Preferably the cassette is constructed of a plastics material as is the lid where applicable. Suitably these parts are constructed by injection moulding a thermoplastics material.

The apparatus for processing or analysing a biological sample may be semi-automatic or automatic. Examples of suitable apparatus include section cutting equipment, embedding equipment, X-ray apparatus and any other histopathology apparatus.

Suitably, the cassette or adaptor according to the invention is substantially transparent to X-rays or other radiation frequencies as desired to allow it to be employed in the examination of samples which are to be examined by irradiation.

Suitably the tissue samples are fixed in a conventional manner, for example using formalin. The sample or specimen is then given a unique identifier which may include a work reference number by a data or records management system. The sample is suitably prepared and inserted into the histology processing cassette and, where used, the lid of the cassette is closed. The sample is then processed, for example by passing one or more organic materials through the sample to remove components of the specimen, for example water and fat, and passing a wax, for example paraffin wax through the sample in preparation for slicing and histological study. The sample or specimen is then suitably placed in a wax mould in an orientation suitable for analysis and encased in molten wax. The mould may comprise a receptacle, suitably of the same shape and dimensions as the cassette whereby the receptacle and cassette fit snugly. The histology processing cassette is suitably then placed on the surface of molten wax in the mould and further wax is added through the cassette. The mould containing the sample and wax together with the cassette is then left to solidify, for example on a cold plate, thereby to encase the sample or specimen.

The sample remains uniquely identifiable during the preparation process and through subsequent analysis. The cassette and also acts as a support structure for mounting the wax block for further processing or analysis, for example in a microtome for sectioning. After sectioning, the wax/specimen section may then be analysed, for example by microscopy.

The histology processing cassette according to the invention has a shallower depth than conventional larger size cassettes which are typically 15 mm deep, and the volume of molten wax required in forming the block assembly is less. Advantageously, the molten wax takes a shorter time to set than for a conventional larger cassette, for example 20 to 40 minutes rather than 1 hour. This enables a higher throughput of mounting blocks for a given volume in a cooler.

Furthermore, the volume of solid wax in the block assembly may be ⅓ to ½ of that in a conventional size wax block and less trimming and therefore shorter processing time, of the mounting block is required.

The mounting block comprises a solid wax part in the mould and a solid wax part in the compartment of the cassette, the two parts being bonded through apertures or perforations in the sample support surface of the cassette. For a given size support surface, a higher proportion of aperture or perforation area advantageously allows thicker wax bonds between the two parts, providing stronger structural integrity.

The present invention is further described by way of example only with reference to the accompanying drawings, in which.

Figure 1:
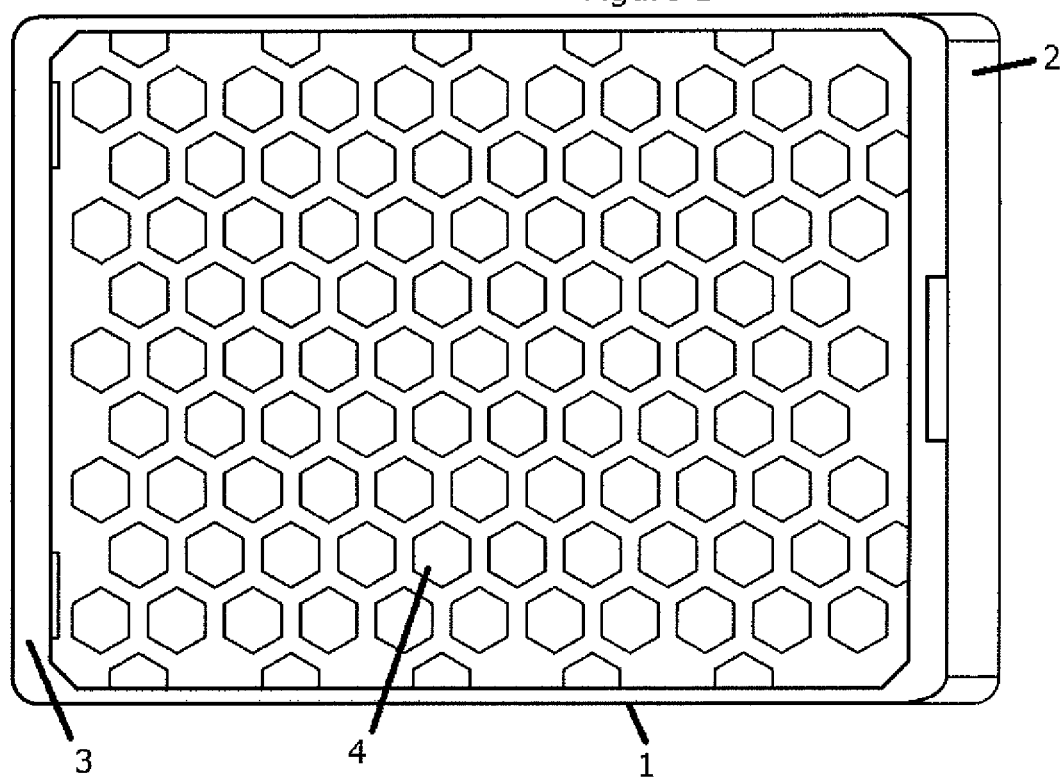
FIG. 1 shows a plan view of a larger sized histology processing cassette without a lid according to the invention.
Figure 2:
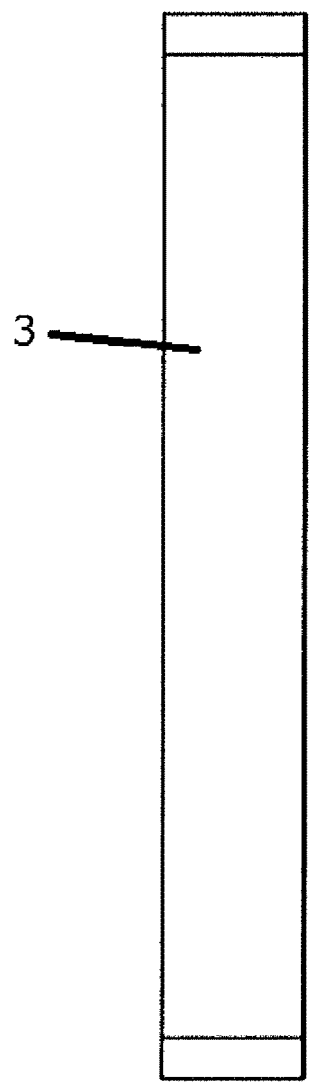
FIG. 2 shows an end elevation of a larger sized histology processing cassette without a lid according to the invention.
Figure 4:
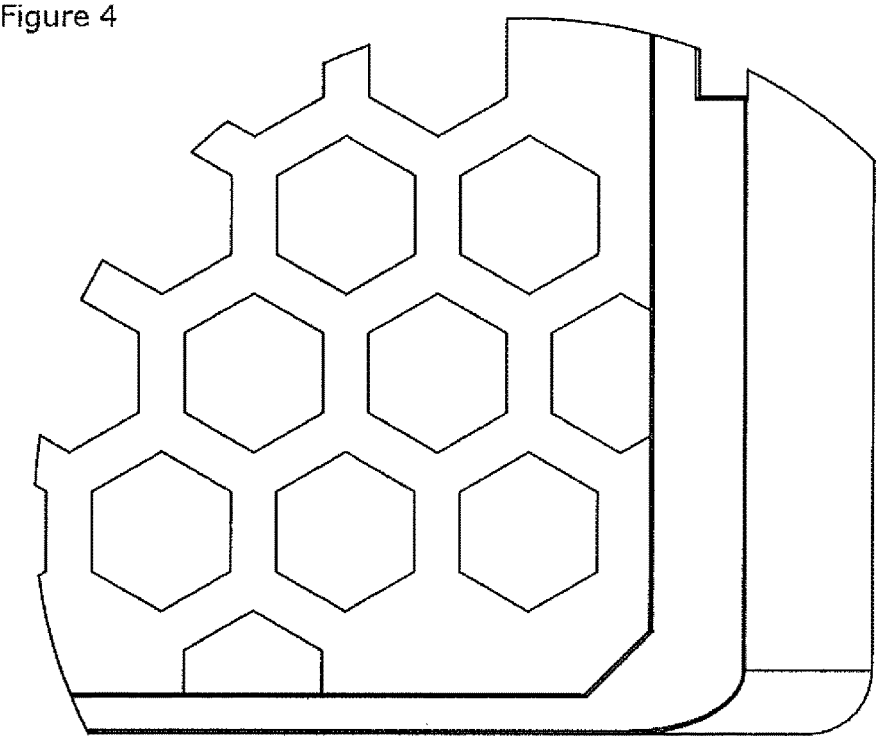
FIG. 4 shows a plan view of a part of the larger sized histology processing cassette shown in FIG. 1.

FIG. 1 shows a histology processing cassette 1 having a sloping front wall 2 and a back wall 3. The sample to be processed is locatable in compartment 4. The cassette has an external length of 75 mm and a depth of 7 mm. FIG. 4, showing a part of the cassette of FIG. 1 shows hexagonal perforations of side 5 mm. FIG. 2 shows a histology processing cassette having a depth of 7 mm and width of 52.5 mm according to the invention.

Figure 3:
FIG. 3 shows a side elevation of a larger sized histology processing cassette without a lid according to the invention.
Figure 5:
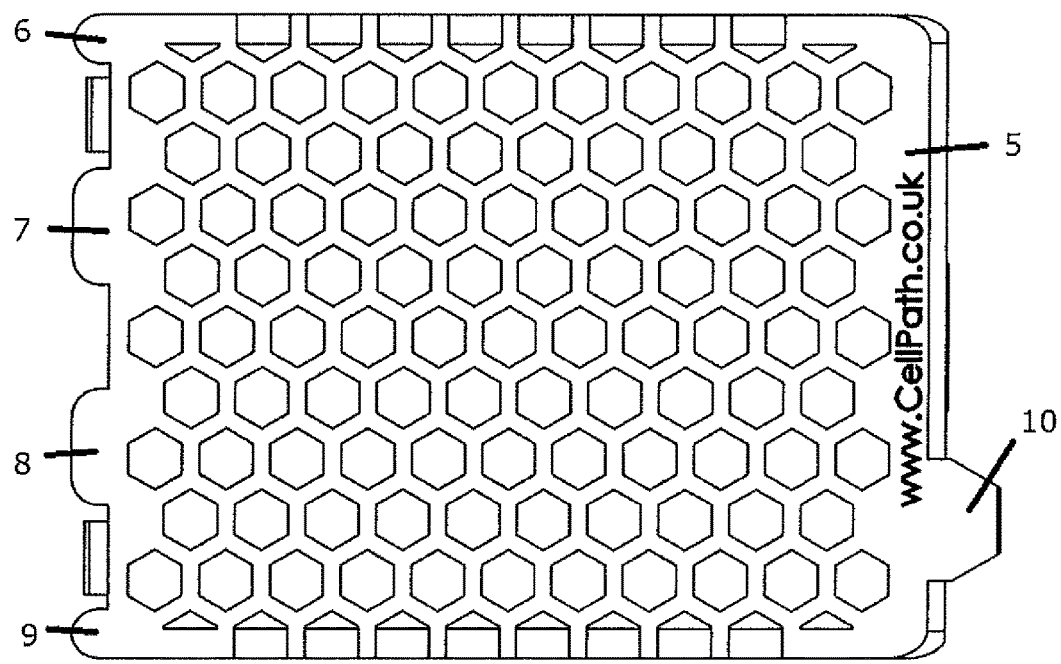
FIG. 5 shows a plan view of a lid for a larger sized histology processing cassette according to the invention.

FIG. 3 shows a side elevation of a cassette according to the invention having a length of 75 mm and depth of 7 mm. The front wall has a vertical part and a sloping or chamfered part, the chamfer being at 32 degrees to the horizontal. FIG. 5 shows a detachable lid 5 for the larger sized cassette having interengaging means 6-10 for engaging with the cassette 1 and for opening the lid.

What is claimed is:

1. A method of avoiding deformation of a biological tissue sample during preparation for analysis comprising:
   i) providing a histology processing cassette comprising a box defining a compartment for holding a biological tissue sample, the box having a bottom face comprising a sample support surface and being transmissible to radiation or a flow of fluid through the face, an open top face, and two side walls, a back wall and a front wall, the box having a length of 65 to 80 mm and width of 50 to 55 mm, being a greater length and width than a standard size histology processing cassette and a depth of 6 to 8 mm being approximately the same as a standard size histology processing cassette, wherein the ratio of the length to the width is approximately from 7 to 8:5, the ratio of the width to the depth is from 6 to 9:1, and the ratio of the length to the depth is from approximately 9 to 12:1, whereby the compartment is adapted to reduce curl of said biological tissue sample in the same dimension as the depth of the compartment;
   ii) placing the sample in the cassette and treating the sample by contacting it with a processing solution; and
   iii) contacting the sample with molten paraffin and cooling the sample in molten paraffin so the sample is embedded in solidified paraffin for further processing.

2. A histology processing cassette comprising a box defining a compartment for holding a biological tissue sample, the box having a bottom face comprising a sample support surface and being transmissible to radiation or a flow of fluid through the face, an open top face, and two side walls, a back wall and a front wall, the box having a length of 65 to 80 mm and width of 50 to 55 mm, being a greater Length and width than a standard size histology processing cassette and a depth of 6 to 8 mm being approximately the same as a standard size histology processing cassette, wherein the ratio of the length to the width is approximately from 7 to 8:5, the ratio of the width to the depth is from 6 to 9:1, and the ratio of the length to the depth is from approximately 9 to 12:1, whereby the compartment is adapted to reduce curl of said biological tissue sample in the same dimension as the depth of the compartment.

3. A cassette according to claim 2 comprising a lid transmissible to radiation or a flow of fluid through the lid for closing the open top face of the cassette.

4. A cassette according to claim 2 in which the box comprises a plurality of compartments defined by at least one partition wall which is generally perpendicular to the bottom face and top face.

5. A cassette according to claim 4 in which the lid is moveable relative to the box of the cassette and is detachable.

6. A cassette according to claim 5 in which the lid is pivotally mounted on the box.

7. A cassette according to claim 6 wherein the lid is adapted in a first configuration to be open wherein the lid is at an angle to the box of less than 170 degrees and in a second configuration to close the compartment.

8. A cassette according to claim 7 wherein the lid is at an angle to the box of 100 to 140 degrees in the first configuration.

9. A cassette according to claim 4 in which the lid is moveable relative to and permanently attached to the box.

* * * * *